US008552850B2

(12) United States Patent
De Mers et al.

(10) Patent No.: US 8,552,850 B2
(45) Date of Patent: Oct. 8, 2013

(54) NEAR-TO-EYE TRACKING FOR ADAPTIVE OPERATION

(75) Inventors: Robert E. De Mers, Nowthen, MN (US); Carl A. Best, Glendale, AZ (US); Frank Cupero, Glendale, AZ (US)

(73) Assignee: Honeywell International Inc., Morristown, NJ (US)

( * ) Notice: Subject to any disclaimer, the term of this patent is extended or adjusted under 35 U.S.C. 154(b) by 613 days.

(21) Appl. No.: 12/707,293

(22) Filed: Feb. 17, 2010

(65) Prior Publication Data

US 2011/0199202 A1    Aug. 18, 2011

(51) Int. Cl.
*B60Q 1/00*    (2006.01)
(52) U.S. Cl.
USPC ............................. 340/439; 340/945; 340/576
(58) Field of Classification Search
USPC ............. 340/945, 576, 439, 546, 156; 345/7; 341/121; 351/210, 246; 359/630
See application file for complete search history.

(56) References Cited

U.S. PATENT DOCUMENTS

| 5,243,339 | A | * | 9/1993 | Graham et al. | 340/945 |
| 5,402,109 | A | | 3/1995 | Mannik | |
| 5,801,667 | A | * | 9/1998 | Shimizu et al. | 345/7 |
| 6,163,281 | A | * | 12/2000 | Torch | 341/21 |
| 6,859,144 | B2 | * | 2/2005 | Newman et al. | 340/576 |
| 6,974,414 | B2 | | 12/2005 | Victor | |
| 2005/0007552 | A1 | * | 1/2005 | Fergason et al. | 351/210 |
| 2006/0203197 | A1 | * | 9/2006 | Marshall | 351/246 |
| 2006/0238877 | A1 | * | 10/2006 | Ashkenazi et al. | 359/630 |
| 2006/0255956 | A1 | * | 11/2006 | Arakawa et al. | 340/576 |
| 2010/0156617 | A1 | | 6/2010 | Nakada et al. | |

FOREIGN PATENT DOCUMENTS

| EP | 2012286 A2 | 1/2009 |
| EP | 2012286 A3 | 6/2010 |
| JP | 06230132 | 8/1994 |

OTHER PUBLICATIONS

Cupero, F., et al.; Head Worn Display System for Equivalent Visual Operations, NASA/CR-2009-215781, Jul. 2009, Phoenix, Arizona.
Valimont, B., et al.; When the Wheels Touch Earth and the Flight is Through, Pilots Find One Eye is Better Than Two, Apr. 2009, Orlando, FL.
EP Search Report, EP 11154222.1-1232 dated Jul. 7, 2011.
EP Communication, EP 11154222.1-1232 dated Jul. 19, 2011.
EP Communication; EP 11154222.1-1232 dated Jan. 2, 2013.

* cited by examiner

*Primary Examiner* — Steven Lim
*Assistant Examiner* — Kaleria Knox
(74) *Attorney, Agent, or Firm* — Ingrassia Fisher & Lorenz, P.C.

(57) ABSTRACT

A method and a system are provided for adaptive vehicle operation. The method includes the steps of sensing a position and an orientation of a near-to-eye display device worn by the vehicle operator, determining a direction of gaze of the vehicle operator in response to the position and the orientation of the near-to-eye display device, and selectively generating an alert signal in response to the direction of gaze of the vehicle operator.

19 Claims, 6 Drawing Sheets

NEAR-TO-EYE TRACKING FOR ADAPTIVE OPERATION

FIELD OF THE INVENTION

The present invention generally relates to user monitoring systems for adaptive operation, and more particularly relates to a method and apparatus for near-to-eye tracking for adaptive operation.

BACKGROUND OF THE INVENTION

As the operation of vehicles such as airplanes becomes more complex, it is preferable that the vehicle operator (e.g., the flight crew) be attentive and receives information in a timely manner to ensure proper operation. One means for providing information is a near-to-eye (NTE) display system. A NTE display system is a type of head worn display (HWD) system which uses a visor, a helmet or a cap to place a display in front of one or both eyes. Typically the NTE display is semi-transparent (such as a liquid crystal display (LCD), liquid crystal on silicon (LCos) display or organic light emitting diode (OLED) display) so that the information presented on the NTE display appears to the user superimposed on the visible scene. For example, a NTE display can provide a three-dimensional view of a scene outside the vehicle for use by the vehicle's operator even in poor visibility conditions, such as thick fog conditions.

Current flight decks have very few sensors that observe the flight crew. In order for NTE display systems to operate properly, additional sensors are required to sense a user's head position and orientation to present appropriate information on the NTE display. Outside their use in the HWD system, these sensors provide the opportunity to collect much more detailed information about pilot state and actions. Recently, proposals have been made to use this information to derive knowledge of the flight crew's state so that decisions can be made about the level of automation suitable for changing circumstances.

Typically, multiple alert devices are located throughout the cockpit. Present vehicle technology does not adapt operation in response to an operator's attention or inattention for proper and safe operation of the vehicle. Thus, what is needed is a monitoring system for alerting a vehicle's operator when his inattention has been detected. In addition, what is needed is an adaptive operation mode for adapting alerts to provide the most timely and most sensible alerts. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method is provided for alerting a vehicle operator. The method includes the steps of sensing a position and an orientation of a near-to-eye display device worn by the vehicle operator, determining a direction of gaze of the vehicle operator in response to the position and the orientation of the near-to-eye display device, and selectively generating an alert signal in response to the direction of gaze of the vehicle operator.

In addition, an attention monitoring system coupled to a near-to-eye display system is provided. The near-to-eye display system senses a position and orientation of a near-to-eye display and generates focus data corresponding to a direction of gaze of a vehicle operator in response to the position and the orientation of the near-to-eye display. The attention monitoring system includes a plurality of alerting devices and a controller. The plurality of alerting devices provides sensible alerts to the vehicle operator. The controller is coupled to the near-to-eye display system and the plurality of alerting devices. The controller receives the focus data from the near-to-eye display system and provides an alert signal to a selected one of the plurality of alerting devices in response to the focus data.

Further, a monitoring system for vehicle operation is provided which includes a near-to-eye display device, one or more sensors and a controller. The near-to-eye display device is worn by an operator of the vehicle. The one or more sensors monitor a position and an orientation of the near-to-eye display system. The controller is coupled to the one or more sensors and determines a direction of gaze of the operator of the vehicle in response to the position and the orientation of the near-to-eye display system. Thereafter, the controller selectively generates an alert signal in response to the direction of gaze of the operator of the vehicle.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
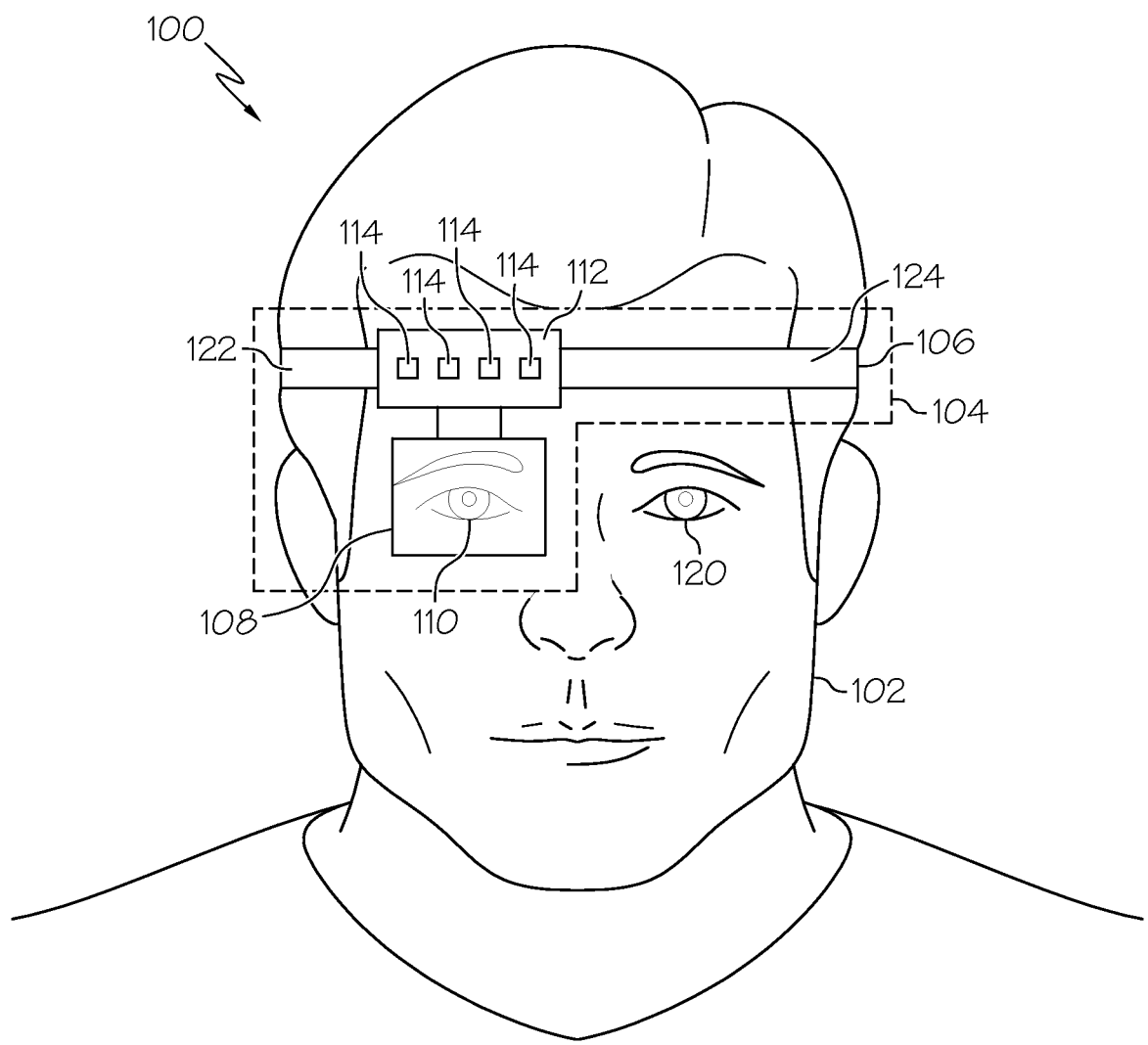
FIG. 1 is a front planar view illustrating a user wearing a near to eye display system in accordance with an embodiment of the present invention.

FIG. 1 depicts an operator 102 of a vehicle, such as a flight crew member of an aircraft, wearing a near-to-eye (NTE) display system 104. The NTE display system 104 includes a headband 106 coupled to a semi-transparent display 108 such that when correctly worn by the operator 102, the semi-transparent display 108 is placed in the line of sight of the right eye 110 at a predetermined distance from the right eye 110. In this manner, information can be presented to the operator 102 on the semi-transparent display 108 superimposed on the visible scene beyond, for example, the controls and other items inside the cockpit and/or the outside view through the window of the cockpit. Infrared light emitting diodes (LEDs) 114 are located on a portion 112 of the headband 106 to sense a direction of gaze of the operator 102 (e.g.

looking up, looking down, looking at one portion of a cockpit or another portion, etc.) at any point in time in order to present appropriate information on the display 108.

Outside their use in the NTE display system 104, the LEDs 114 are utilized to provide more detailed information about the state and actions of the operator 102. In accordance with the present embodiment, the NTE display system 104 is configured to monitor the head position of operator 102 by monitoring the position and orientation of the NTE display device (i.e., the NTE display system 104). In this manner, the operator's direction of gaze at any point in time can be sensed for generation and presentation of an appropriate transparent view including conformal graphics and/or other information on the display 108.

The configuration of the NTE display system 104 is not limited to the device shown in the view 100. For example, while the NTE display system 104 is a monocular NTE display system, a binocular NTE display system could also be employed in the present embodiment. In addition, while the monocular NTE display system 104 in accordance with the present embodiment has the display 108 situated over the right eye 110, the present embodiment could also use a monocular NTE display system having the display positioned in the line of sight of the left eye 120. Further, while the LEDs 114 are incorporated in the portion 112 of the headband 106, the number and location of the LEDs 114 can be anywhere on the headband 106, such as in portion 122 or portion 124, or even located around the display 108.

The LEDs 114 are infrared in order to emit wavelengths not visible to the operator 102 and thereby not interfere with operation of the aircraft and/or the view of the operator 102. In addition, the LEDs 114 are positioned on the headband 106 to allow sensing of the position and orientation of the NTE display system 104. The present embodiment, however, is not limited to the use of infrared LEDs or, in fact, is not limited to the use of LEDs 114, and may include any reflective or emissive device attachable to the NTE display system 104 that would allow sensing of the position and orientation of the NTE display system 104 and, consequently, determination of the direction of gaze or focus of the pilot.

Figure 2:
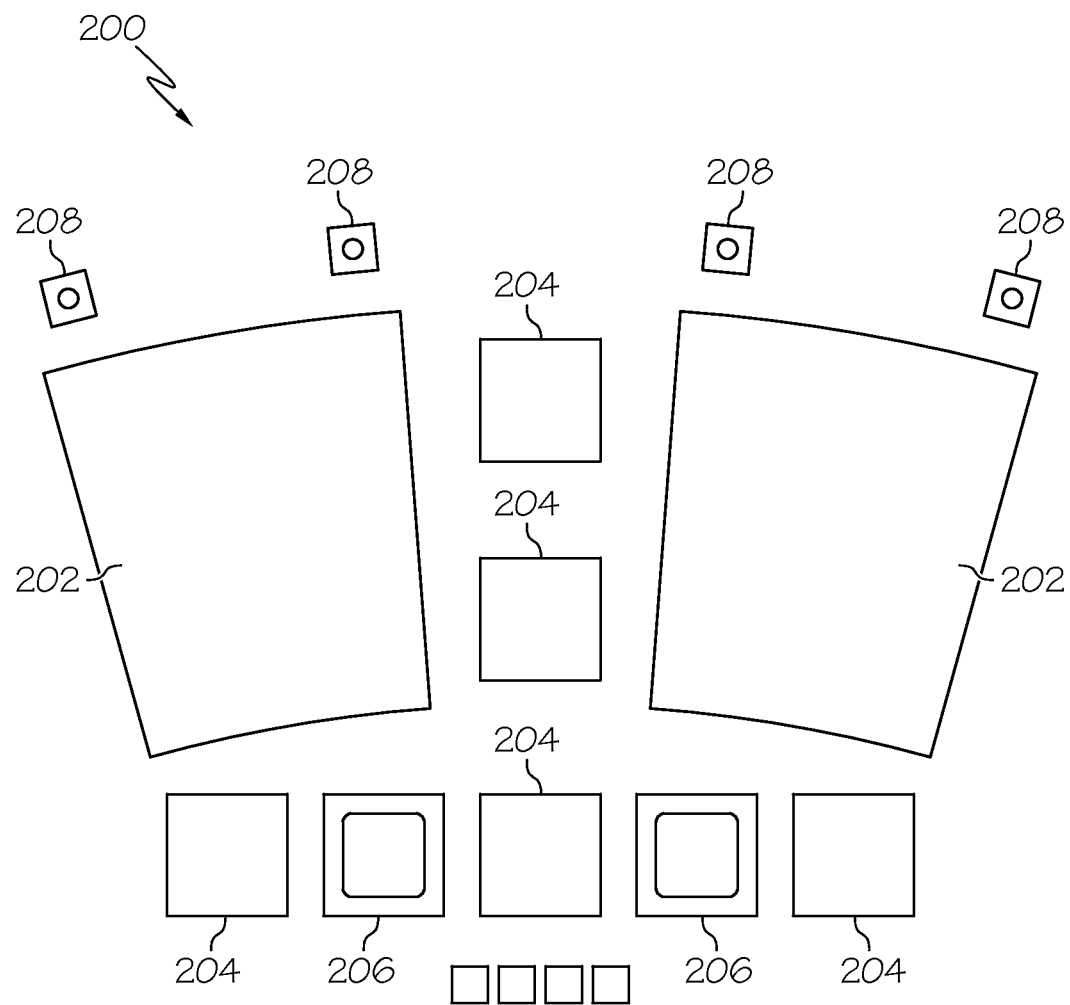
FIG. 2 is a top front left perspective view illustrating a portion of an aircraft cockpit and a monitoring system for monitoring a position of the near to eye display system of FIG. 1 in accordance with the present embodiment.

Referring to FIG. 2, a top front left perspective view 200 illustrates a portion of an aircraft cockpit in accordance with the present embodiment. Windows 202 allow the operator 102 to view conditions and terrain outside the aircraft. Controls and alert devices are arranged in areas 204 of the cockpit, including display monitors 206 for presenting textual and visual information. In order to render conformal graphics on the display 108 (FIG. 1), the outputs of multiple NTE sensors 208 located throughout the cockpit are analyzed to determine head position and orientation of the operator 102 by determining the position and orientation of the NTE display system 104. The information sensed by the NTE sensors 208 is used to determine if the operator 102 is looking out the window, at the in-cockpit controls or displays in areas 204, or at some other point of interest.

In accordance with the present embodiment, the NTE sensors 208 are infrared sensors designed to receive emissions from the infrared LEDs 114 in order to determine the position of the NTE display system 104 and, thereafter, the direction of gaze. Instead of infrared sensors, the NTE sensors 208 could be cameras for tracking and analyzing positions of the NTE display system 104.

Figure 3:
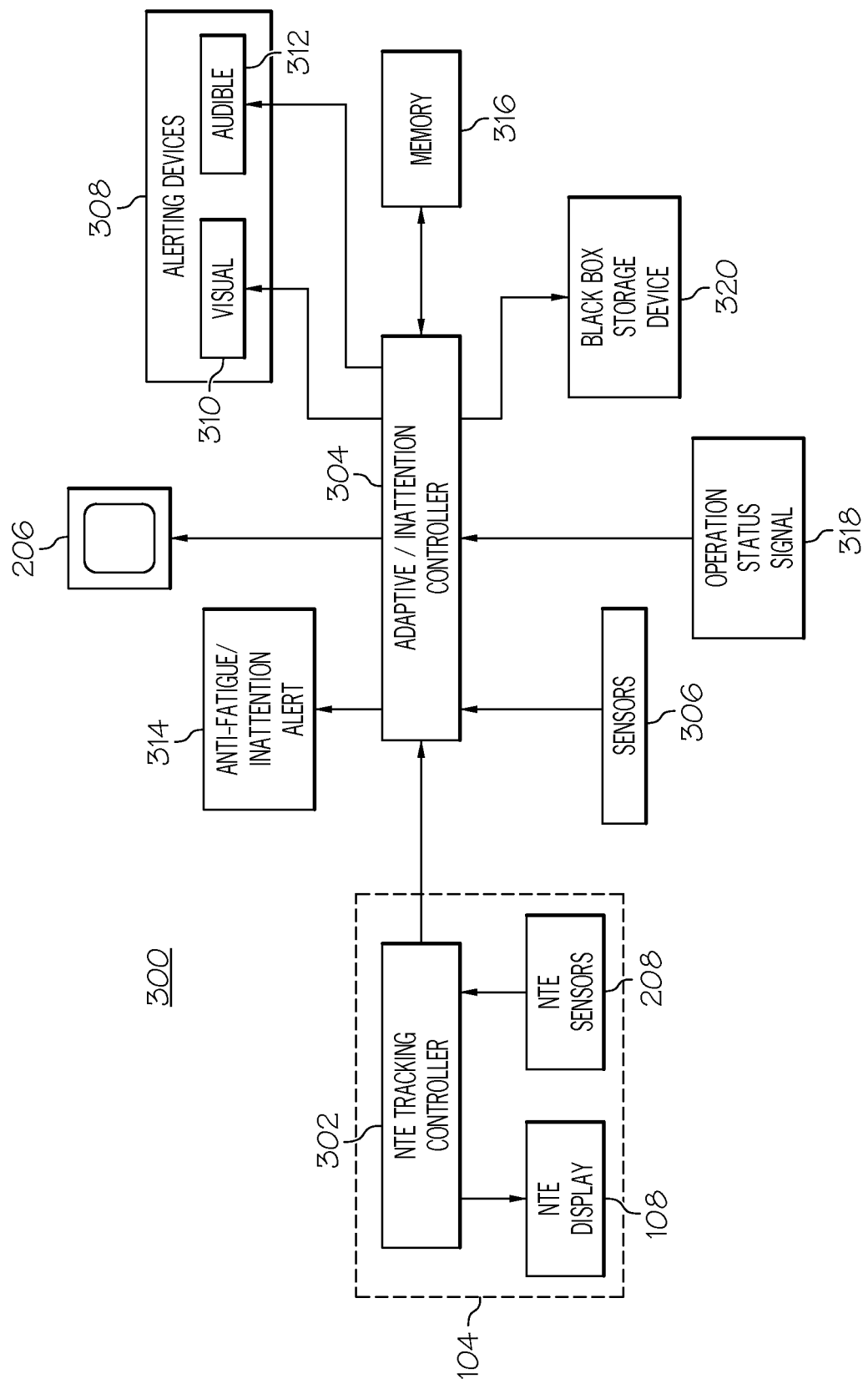
FIG. 3 is a block diagram of a system utilizing the near to eye display system of FIG. 1 in accordance with the present embodiment.

FIG. 3 depicts a block diagram of a system 300 for vehicle operation in accordance with the present embodiment. The NTE display system 104 includes the display 108, the NTE sensors 208 and a NTE tracking controller 302. The NTE tracking controller 302 receives signals from the NTE sensors 208, such as cockpit cameras or infrared sensors, and generates signals which are provided to the display 108. The signals present appropriate information on the display 108 for generating the view of conformal graphics or other information for presentation to the operator 102.

In accordance with the present embodiment, the NTE tracking controller 302 also generates focus data corresponding to the direction of gaze of the operator 102 in response to the information monitored by the NTE sensors 208 (i.e., whether the operator 102 is looking out the window 202, at the in-cockpit displays 206, at the areas 204 including various controls and alerts, or at some other point of interest). The NTE tracking controller 302 is coupled to an adaptive/inattention controller 304 for providing the focus data corresponding to the direction of gaze of the operator 102 thereto. The focus data (e.g., the operator head tracking data resulting from monitoring the position and orientation of the NTE display system 104) is utilized by the adaptive/inattention controller 304 for multiple purposes.

First, the focus data is used for initiating a change in system operation and/or adaptive operation of cockpit alerting devices. Additional avionics sensors 306 which, when triggered, trigger/initiate a change in system operation or provide operator sensible alerts to the flight crew, are coupled to the adaptive/inattention controller 304. A change in system operation may include changing the information and or visual presentation on one of the display monitors 206 or moving a visual presentation of flight information from one of the display monitors 206 to another one of the display monitors 206. The adaptive/inattention controller 304 may initiate such change in system operation in response to the focus data corresponding to the direction of gaze of the operator 102 received from the NTE controller 302.

Operator sensible alerts are alerts that can be sensed by an operator, such as visual or audible alerts. Since the focus data indicates where the pilot's head (and potentially direction of gaze) are pointed, the adaptive/inattention controller 304 decides where and/or how to present an alert to warn the operator 102 of a dangerous condition. Therefore, when the avionics sensors 306 are triggered, an alert signal is provided to the adaptive/inattention controller 304. The adaptive/inattention controller 304 then activates one or more of several cockpit alerting devices 308 selected in response to the focus data corresponding to the direction of gaze of the operator 102.

As described above, the cockpit alerting devices 308 may include visual alerting devices 310 and audible alerting devices 312 in one or more areas 204 of the cockpit. The adaptive/inattention controller 304 determines whether to provide the alert signal to one of the visual alerting devices 310 and/or one of the audible alerting devices 312 in response to the direction of gaze of the operator 102 by selecting between the visual alerting devices 310 and the audible alerting devices 312 in response to the focus data received from the NTE tracking controller 302. Accordingly, a visual alert could be repositioned from one of the visual alerting devices 310 to another one of the visual alerting devices 310 within the direction of focus or gaze of the operator 102 as determined by the focus data. Alternatively or additionally, the adaptive/inattention controller 304 may decide to present an audible tone from one of the audible alerting devices 312 rather than a flashing light from a visual alerting device 310 to warn the operator 102 of a dangerous condition.

In addition, if the NTE tracking controller 302 determines that the focus of the operator 102 is on a display monitor 206, the adaptive/inattention controller 304 may determine to provide the alert signal to the operator 102 by providing signals to the display monitor 206 to present an alert message on the display monitor 206 in response to the focus data received from the NTE tracking controller 302. For example, in a training situation, the operator 102 could be directed to modify his/her instrument scanning pattern or crew coordination techniques by a message and/or instructions on the display monitor 206. The alert message on the display monitor 206 could be a specific alphanumeric message or could be a change of the visual presentation or any portion thereof, such as a change of the background, a change of the color, or a flashing of the visual presentation).

In accordance with the present embodiment, the focus data is also used for monitoring attention of the operator 102 by monitoring the focus data for a predetermined time. As described above, the focus data provided by the NTE tracking controller 302 to the adaptive/inattention controller 304 corresponds to the position and orientation of the NTE display system 104 or a portion thereof and, over time, corresponds to head tracking data which measures the direction of gaze of the operator 102 and an amount of change in the direction of gaze of the operator during such time. The head tracking data is then compared to a pilot state model operating within the adaptive/inattention controller 304. Thus, if the operator 102 is inattentive by not focusing on appropriate cockpit areas 204 for the predetermined time, an inattention signal is provided by the adaptive/inattention controller 304 to an anti-fatigue/inattention alerting device 314 (e.g., one of the audible alerting devices 312) to alert the operator 102 to, for example, look out window 202 and/or check instruments. Also, if the adaptive/inattention controller 304 determines from the head tracking data that an attention level of the operator 102 for the predetermined time is below a threshold attention level, the inattention signal is provided by the adaptive/inattention controller 304 to the anti-fatigue/inattention alerting device 314.

In addition, the length of the predetermined time or threshold attention level can be made context dependent. For example, in close proximity to an airport, the inattention time may be much less than while in high-altitude cruise. Thus, the predetermined time for measuring inattention and/or the threshold attention level can be selected by the adaptive/inattention controller 304, from a plurality of predetermined monitoring times stored in a memory 316, in response to the aircraft operation as indicated by an operation status signal 318 received from one or more operational controllers (not pictured).

Further, in accordance with the present embodiment, the focus data is used to augment the flight data recorder and voice recorder. The adaptive/inattention controller 304 is coupled to a black box storage device 320 for storage of the focus data in order to maintain a record of the direction of gaze of the operator 102 and enable retrieval of the focus data after a notable event.

In the system 300, the NTE tracking controller 302 for determining the focus of the operator 102 and the adaptive/inattention controller 304 for controlling the alert operation of the aircraft are depicted as two separate controllers. For distributed operation, separate controllers would be appropriate. However, the present embodiment is not limited to such distributed computing and those skilled in the art will realize that both determining the focus of the operator 102 and controlling the alert operation of the aircraft could be implemented in a single controller.

Figure 4:
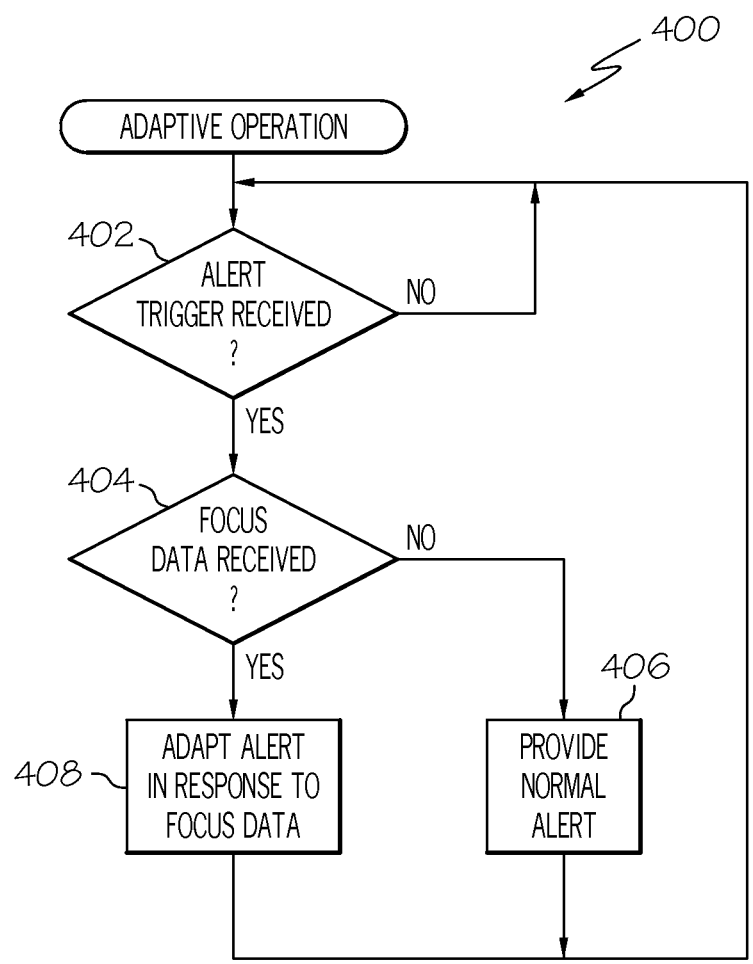
FIG. 4 is a flowchart depicting an adaptive alerting method in accordance with the present embodiment.

Referring next to FIG. 4, a flowchart 400 depicts an adaptive alerting operation of the adaptive/inattention controller 304 in accordance with the present embodiment, which adapts the position or nature of an alert in response to focus data which indicates an area of gaze or focus of an operator. Initially, operation of the adaptive/inattention controller 304 determines whether a signal has been received from one of the avionics sensors 306 indicating that such avionics sensor 306 has been triggered (402). When such avionics sensor 306 has been triggered, the adaptive/inattention controller 304 determines whether focus data has been received from the NTE tracking controller 302 (404). If no focus data has been received, an alert is presented in accordance with the normal alerting method (406) by activating the appropriate one of the alerting devices 308, such as a visual alerting device 310. If focus data has been received, alerting is adapted in response to the focus data (408) by activating an alternate one of the alerting devices 308, such as activating an alternate visual alerting device 310 within the gaze or focus of the operator 102 as indicated by the focus data and/or activating one of the audible alerting devices 312 instead of the appropriate visual alerting device 310. After the alerting device 308 is activated 406, 408, processing returns to await triggering of a next one of the avionics sensors 306.

Figure 5:
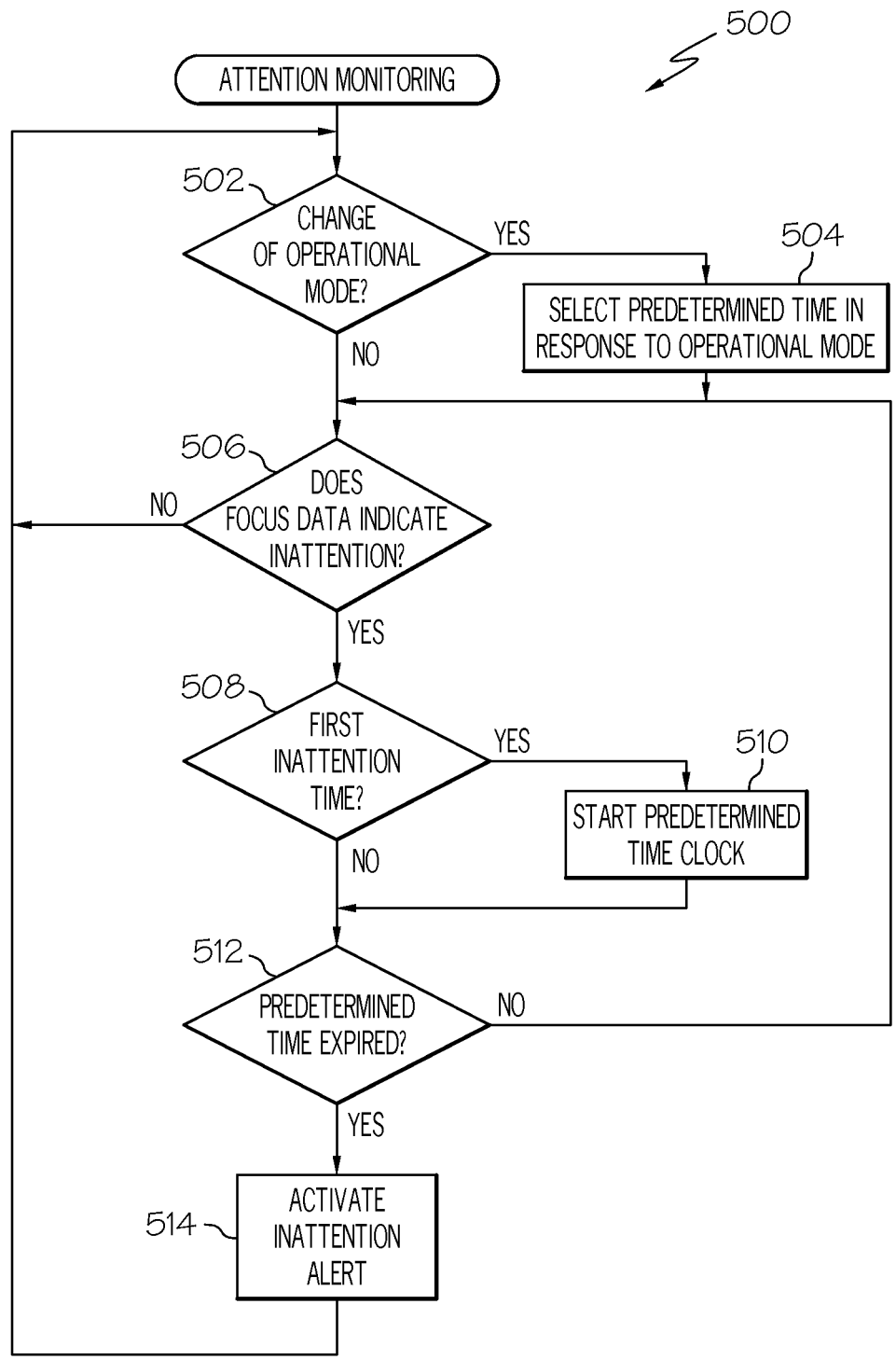
FIG. 5 is a flowchart depicting an inattention monitoring operation in accordance with the present embodiment.

FIG. 5 is a flowchart 500 of a method of inattention monitoring carried out by the adaptive/inattention controller 304 in accordance with the present embodiment. Initially, it is determined whether the operational mode (e.g., whether the aircraft is approaching an airport for landing, whether the aircraft is cruising at a high altitude, or another predefined operational mode) has changed (502). If the operational mode has changed, one of a plurality of predetermined times for measuring focus data stored in the memory 316 is selected (504) in response to the new operational mode. In this manner, different predetermined times to measure inattention are utilized during different operational modes (e.g., a shorter lack of attention time when the aircraft is approaching an airport for landing or a longer lack of attention time when the aircraft is cruising at a high altitude on autopilot).

Utilizing the newly selected predetermined time or a previously selected predetermined time, the focus data received from the NTE tracking controller 302 is examined to determine if inattention is indicated (506). If the focus data indicates that the operator is paying attention to the appropriate cockpit areas 204 (506), the process returns to determine if the operational mode has changed (502).

When the focus data indicates inattention (506), the process determines whether this is a first determination of inattention after previously determining that the operator 102 is paying attention (506). If the determination of inattention is a first determination of inattention, a predetermined time countdown clock is started to measure passing of a predetermined time period (510). Either after the predetermined time countdown clock is started or after a second or subsequent consecutive determination of inattention (508), the process determines whether the selected predetermined time period has passed (512). When the selected predetermined time period has passed, the fatigue/inattention alert is activated by providing an inattention signal to the anti-fatigue/inattention alerting device 314 to provide a cautionary audible tone for alerting the operator 102 to, for example, look out the window 202 and check instruments (514). Until the selected predetermined time period has passed, the process continues to monitor the attention of the operator 102 (506).

As discussed above in regards to FIG. 3, the adaptive/inattention controller 304 stores all focus data received in the black box storage device 320 during both attention monitoring operation (FIG. 5) and adaptive operation (FIG. 4) so that the focus data augments the flight data recorder and voice recorder.

Figure 6:
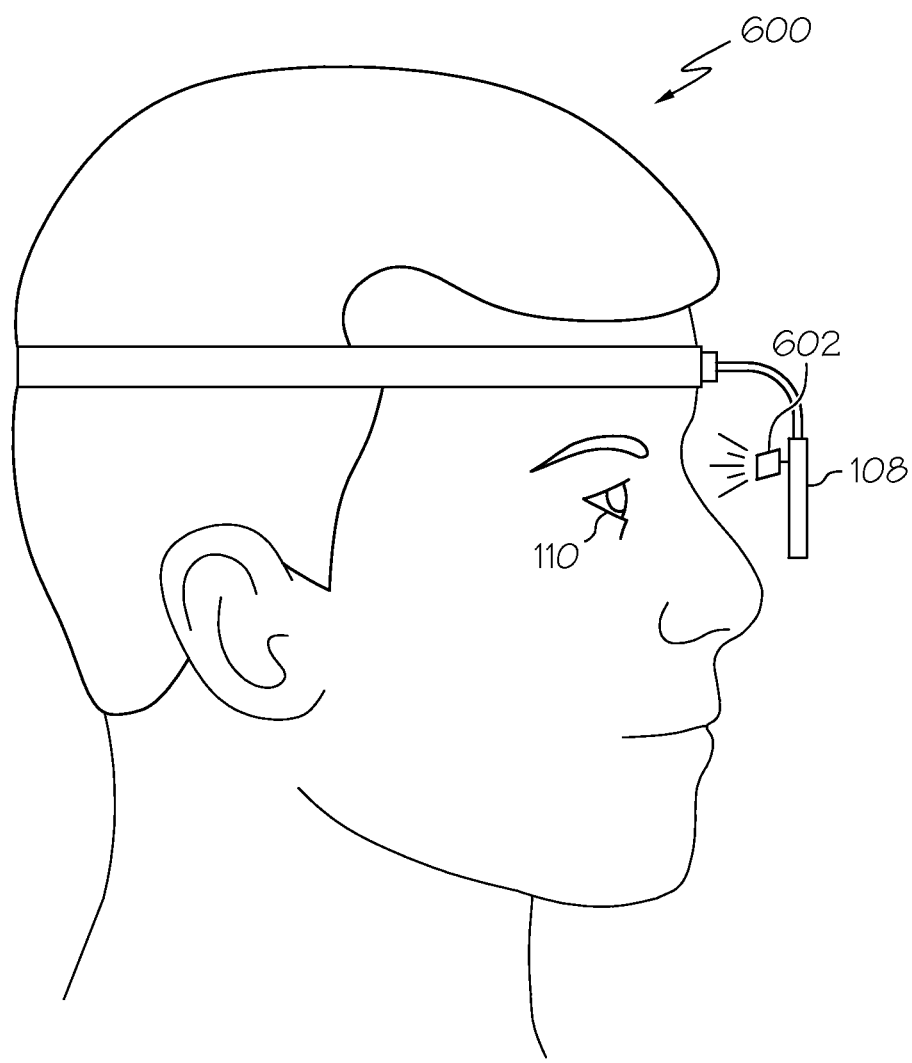
FIG. 6 is a side planar view illustrating the near to eye display system of FIG. 1 in accordance with an alternate embodiment.

Referring to FIG. 6, a side planar view 600 depicts a portion of the NTE display system 104. The display 108 is shown positioned in front of the eye 110 of the operator 102. In accordance with conventional operation of the NTE display system 104, a camera 602 is mounted on the display 108 and focused on the eye 110 to track eye movements and measure pupil diameter, the camera 602 providing this information as signals to the NTE controller 302. The NTE controller 302 uses the signals tracking eye movements as additional focus data and, along with signals from the NTE sensors 208, utilizes the focus data to generate the view of conformal graphics or other information presented on the display 108. In addition, the NTE controller 302 uses the signals corresponding to pupil diameter for adjustment of the brightness of the view of conformal graphics or other information presented on the display 108.

In accordance with an alternate embodiment, the signals from the camera 602 monitoring eye activity may be utilized to improve attention and fatigue monitoring. For example, it is well known that fatigue of the operator 102 can be determined by measuring eye-blinks. The information recorded by the camera 602 can be utilized to measure eye-blinks and this eye-blink information can be provided to the adaptive/inattention controller 304 for fatigue/inattention determination. Along the same lines, it is well known that head nods, which can be detected by the NTE sensors 208, are also a measure of fatigue and such information can also be provided to the can be provided to the adaptive/inattention controller 304 for improved fatigue/inattention determination.

Thus it can be seen that a method and system for attention monitoring which alerts an operator 102 when determining his inattention and/or fatigue has been provided. In addition, a method and system for an adaptive operation mode for adapting alerts to provide the most timely and most sensible alerts has been provided. Also, a method and system for monitoring and securely storing focus information indicating where the flight crew is looking has been provided to aid in post accident scenario recreation. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A method of alerting a vehicle operator comprising:
sensing a position and an orientation of a near-to-eye display device worn by the vehicle operator;
determining a direction of gaze of the vehicle operator in response to the position and the orientation of the near-to-eye display device;
selectively generating an alert signal in response to the direction of gaze of the vehicle operator; and
estimating an attention level of the vehicle operator in response to the determined direction of gaze and an amount of change of the direction of gaze during a predetermined time period, and wherein the step of selectively generating the alert comprises generating an inattention alert signal in response to the estimated attention level being below a threshold attention level.

2. The method in accordance with claim 1 wherein the alert signal is an inattention alert signal, and wherein the step of selectively generating the alert signal comprises selectively generating the inattention alert signal further in response to measurement of passing of a selected one of a plurality of predetermined time periods, each of the plurality of predetermined time periods associated with one of a plurality of vehicle operation modes.

3. The method in accordance with claim 1 further comprising storing information corresponding to the direction of gaze of the vehicle operator.

4. The method in accordance with claim 1 wherein the step of sensing the position and the orientation of the near-to-eye display device comprises sensing using at least one sensor.

5. The method in accordance with claim 1 wherein the step of sensing the orientation of the near-to-eye display device comprises sensing an output of at least one infrared light emitting diode affixed to the near-to-eye display device.

6. The method in accordance with claim 1 further comprising the step of initiating a change in system operation in response to the determined direction of gaze of the vehicle operator.

7. The method in accordance with claim 1 wherein the step of selectively generating the alert signal comprises initiating an alert with a selected one of a plurality of alerting devices, the selected one of the plurality of alerting devices selected at least in part in response to the determined direction of gaze of the vehicle operator.

8. The method in accordance with claim 7 wherein the plurality of alerting devices includes at least one visual alerting device and at least one audible alerting device, and wherein the step of selectively generating the alert signal comprises initiating the alert with a selected one of the at least one visual alerting device or a selected one of the at least one audible alerting device in response to the determined direction of gaze of the vehicle operator.

9. The method in accordance with claim 1 wherein the step of selectively generating the alert signal comprises:
initiating an alert with an alerting device when the direction of gaze of the vehicle operator is determined to be away from a display monitor; and
initiating provision of alert information on the display monitor when the direction of gaze of the vehicle operator is determined to be towards the display monitor.

10. An attention monitoring system coupled to a near-to-eye display system which senses a position and orientation of a near-to-eye display device and generates focus data corresponding to a direction of gaze of a vehicle operator in response to the position and the orientation of the near-to-eye display device, the vehicle monitoring system comprising:
a plurality of alerting devices for providing sensible alerts to the vehicle operator; and
a controller coupled to the near-to-eye display system for receiving the focus data therefrom and coupled to the plurality of alerting devices, providing an alert signal to a selected one of the plurality of alerting devices in response to the focus data, and estimating an attention level of the vehicle operator in response to the determined direction of gaze and an amount of change of the direction of gaze during a predetermined time period, and wherein the step of selectively generating the alert comprises generating an inattention alert signal in response to the estimated attention level being below a threshold attention level.

11. The attention monitoring system in accordance with claim 10 further comprising a memory device for storing a plurality of predetermined time periods, wherein each of the plurality of predetermined time periods is associated with one of a plurality of vehicle operation modes, and wherein the controller is further coupled to the memory device for generating an inattention alert signal and providing the inattention alert signal to one of the plurality of alerting devices in response to measurement of passing of a selected one of the plurality of predetermined time periods, the selected one of the plurality of predetermined time periods selected in response to a present vehicle operation mode.

12. The attention monitoring system in accordance with claim 10 further comprising a black box storage device, wherein the controller is coupled to the black box storage device and stores the focus data in the black box storage device as it is received from the near-to-eye-display system.

13. A monitoring system comprising:
a near-to-eye display device worn by an operator of a vehicle;
one or more sensors for monitoring a position and an orientation of the near-to-eye display device; and
a controller coupled to the one or more sensors for determining a direction of gaze of the operator of the vehicle in response to the position and the orientation of the near-to-eye display device, for selectively generating an alert signal in response to the direction of gaze of the operator of the vehicle, and for estimating an attention level of the vehicle operator in response to the determined direction of gaze and an amount of change of the direction of gaze during a predetermined time period, and wherein the step of selectively generating the alert comprises generating an inattention alert signal in response to the estimated attention level being below a threshold attention level.

14. The monitoring system in accordance with claim 13 further comprising a data storage device coupled to the controller for storing information corresponding to the direction of gaze of the operator.

15. The monitoring system in accordance with claim 13 further comprising:
a memory device coupled to the controller for storing a plurality of predetermined monitoring times, each of the plurality of predetermined monitoring times corresponding to one of a plurality of vehicle operation modes of the vehicle; and
an inattention alerting device for presenting an operator sensible alert in response to receiving an inattention signal from the controller,
wherein the controller determines inattention of the operator of the vehicle and provides the inattention signal to the inattention alerting device in response to the direction of gaze of the operator determined while monitoring the position and the orientation of the near-to-eye display device during a selected one of the plurality of predetermined monitoring times, the controller selecting the one of the plurality of predetermined monitoring times in response to a present vehicle operation mode of the vehicle.

16. The monitoring system in accordance with claim 13 further comprising a plurality of alerting devices for presenting operator sensible alerts when activated by an alert signal from the controller, wherein the controller selects which of the plurality of alerting devices to provide the alert signal to in response to the direction of gaze of the operator of the vehicle.

17. The monitoring system in accordance with claim 16 wherein the plurality of operator alerting devices comprise at least one visual alerting device and at least one audible alerting device.

18. The monitoring system in accordance with claim 16 further comprising a display for displaying visible information to the operator of the vehicle, wherein the controller is coupled to the display and provides an alert to the operator by providing the alert signal to one of the operator alerting devices in response to determining that the direction of gaze of the operator is away from the display, the controller providing the alert to the user by providing signals to the display to present an alert on the display in response to determining that the direction of gaze of the operator is toward the display.

19. The monitoring system in accordance with claim 13 further comprising a black box storage device, wherein the controller is coupled to the black box storage device and stores data in the black box storage device corresponding to the direction of gaze of the operator of the vehicle.

* * * * *